US00PP28397P3

(12) United States Plant Patent
Smulders

(10) Patent No.: US PP28,397 P3
(45) Date of Patent: Sep. 19, 2017

(54) APPLE TREE NAMED 'WUR37'

(50) Latin Name: *Malus domestica*
Varietal Denomination: WUR37

(71) Applicant: STICHTING DIENST LANDBOUWKUNDIG ONDERZOEK - PPO/PRI, Wageningen (NL)

(72) Inventor: Rene Smulders, Wageningen (NL)

(73) Assignee: Stichting Dienst Landbouwkundig Onderzoek-PPO/PRI, Wageningen (NL)

( * ) Notice: Subject to any disclaimer, the term of this patent is extended or adjusted under 35 U.S.C. 154(b) by 0 days.

(21) Appl. No.: 14/998,739

(22) Filed: Feb. 9, 2016

(65) Prior Publication Data

US 2017/0231136 P1 Aug. 10, 2017

(51) Int. Cl.
*A01H 5/08* (2006.01)

(52) U.S. Cl.
USPC ..... Plt./161

(58) Field of Classification Search
USPC ..... Plt./161
See application file for complete search history.

(56) References Cited

PUBLICATIONS

PLUTO Plant Variety Database Jan. 17, 2017. p. 1.*

* cited by examiner

*Primary Examiner* — Annette Para
(74) *Attorney, Agent, or Firm* — C. A. Whealy

(57) ABSTRACT

A new and distinct cultivar of Apple tree named 'WUR37', characterized by its upright plant habit; vigorous growth habit; numerous fruit produced per plant; fruits with red-colored skin spotted with lenticels; resistance to Apple Scab; and suitability for organic farming practices.

2 Drawing Sheets

Botanical designation: *Malus domestica.*
Cultivar denomination: 'WUR37'.

BACKGROUND OF THE INVENTION

The present invention relates to a new and distinct cultivar of Apple tree, botanically known as *Malus domestica* and hereinafter referred to by the name 'WUR37'.

The new Apple tree is a product of a planned breeding program conducted by the Inventor in Elst, Gelderland, The Netherlands. The objective of the breeding program was to create new Apple trees that produce numerous red-colored fruits that are resistant to Apple Scab (*Venturia inaequalis*), a fungus, which causes severe surface blemishing of the fruit and are suitable for organic farming practices.

The new Apple tree originated from a cross-pollination conducted by the Inventor in Elst, Gelderland, The Netherlands in 1993 of *Malus domestica* 'Elise', not patented, as the female, or seed, parent with a proprietary selection of *Malus domestica* identified as code number 1984-015-017, not patented, as the male, or pollen, parent. The new Apple tree was discovered and selected by the Inventor as a single plant within the progeny of the stated cross-pollination grown in a controlled environment in Elst, Gelderland, The Netherlands in 2005.

Asexual reproduction of the new Apple tree by grafting in a controlled environment in Elst, Gelderland, The Netherlands since 2006 has shown that the unique features of this new Apple tree are stable and reproduced true to type in successive generations.

SUMMARY OF THE INVENTION

The new Apple tree has not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WUR37'. These characteristics in combination distinguish 'WUR37' as a new and distinct Apple tree:

1. Upright plant habit.
2. Vigorous growth habit.
3. Numerous fruit produced per plant.
4. Fruits with red-colored skin spotted with lenticels.
5. Resistant to Apple Scab.
6. Suitable for organic farming practices.

The new Apple tree differs primarily from trees of the female parent , 'Elise' in fruit color and Apple Scab resistance as trees 'Elise' produce darker red-colored fruits than trees of the new Apple tree and trees of 'Elise' are not resistant to Apple Scab. Additionally, trees of the new Apple are more suitable for organic farming practices than trees of the female parent selection.

The new Apple tree differs primarily from trees of the male parent selection in growth habit and fruit production as trees of the male parent selection are less vigorous and produce less fruit per tree than trees of the new Apple tree. Additionally, trees of the new Apple are more suitable for organic farming practices than trees of the male parent selection.

Plants of the new *Malus* can be compared to plants of *Malus domestica* 'WUR200', disclosed in a U.S. Plant Patent application filed on Nov. 14, 2015. In side-by-side comparisons conducted in Elst, Gelderland, The Netherlands, the new Apple tree differed primarily from trees of 'WUR200' in the following characteristics:

1. Trees of the new Apple tree were more vigorous and more freely branching than trees of 'WUR200'.
2. Trees of the new Apple tree produced larger and heavier fruits than trees of 'WUR200'.

BRIEF DESCRIPTION OF THE PHOTOGRAPHS

The accompanying photographs illustrate the overall appearance of the new Apple tree showing the colors as true as it is reasonably possible to obtain in colored reproductions of this type. Colors in the photographs may differ slightly from the color values cited in the detailed botanical description which accurately describe the colors of the new Apple tree.

The photograph on the first sheet comprises a side perspective view of a typical tree of 'WUR37' grown in an outdoor orchard.

The photograph on the second sheet is a close-up view of typical fruiting branch of 'WUR37'.

DETAILED BOTANICAL DESCRIPTION

The aforementioned photographs, following observations and measurements describe trees grown during the summer in Randwijk, Gelderland, The Netherlands in an outdoor orchard and under cultural practices typical of commercial Apple tree production. Trees were four years old when the photographs and description were taken. Measurements and numerical values represent averages for typical trees and tree parts. The actual measurements of any individual tree or tree parts, or any group of trees or tree parts, of the new Apple tree may vary from the stated average. In the following description, color references are made to The Royal Horticultural Society Colour Chart, 2001 Edition, except where general terms of ordinary dictionary significance are used.

Botanical classification: *Malus domestica* 'WUR37'.

Parentage:

*Female, or seed, parent.*—*Malus domestica* 'Elise', not patented.

*Male, or pollen, parent.*—Proprietary selection of *Malus domestica* identified as code number 1984-015-017, not patented.

Propagation:

*Type.*—Typically by grafting onto a rootstock.

Plant description:

*Plant and growth habit.*—Upright plant habit and vigorous growth habit.

*Tree height.*—About three meters.

*Tree diameter.*—About 80 cm to 150 cm.

*Growth rate.*—About 20 cm to 30 cm per year.

*Trunk description.*—Diameter: About 5 cm to 7 cm. Strength: Strong. Texture: Slightly rough, woody. Color: Close to 200A.

*Lateral branch description.*—Length: About 40 cm to 70 cm. Diameter: About 3 cm to 5 cm. Internode length: About 2 cm to 4 cm. Strength: Strong, firm. Angle of attachment: About 80° from main trunk axis. Texture: Pubescent, woody. Color: Close to 200A.

*Leaf description.*—Arrangement: Alternate; simple. Length: About 7 cm to 10 cm. Width: About 3 cm to 5 cm. Shape: Elliptic. Apex: Acute. Base: Cordate, blunt. Margin: Serrate. Texture, upper surface: Smooth, glabrous. Texture, lower surface: Rough, pubescent. Venation pattern: Pinnate. Color: Developing and fully developed leaves, upper surface: Close to 137A; venation, close to 146D. Developing and fully developed leaves, lower surface: Close to 146A; venation, close to 146D. Petioles: Length: About 5 cm to 9 cm. Diameter: About 5 mm. Texture, upper and lower surfaces: Smooth, glabrous. Color, upper and lower surfaces: Close to 146D.

Flower description:

*Flower type and flowering habit.*—Single rotate flowers arranged on panicles; freely flowering habit with about six to ten flowers per inflorescence; flowers face mostly outwardly.

*Fragrance.*—Faintly fragrant, pleasant.

*Natural flowering season.*—Continuously flowering in April and May in The Netherlands.

*Flower longevity.*—Flowers last about two weeks on the plant; flowers not persistent.

*Inflorescence height.*—About 3 cm to 5 cm.

*Inflorescence diameter.*—About 3 cm to 5 cm.

*Flower diameter.*—About 2 cm to 3 cm.

*Flower depth (height).*—About 5 mm to 10 mm.

*Flower buds.*—Shape: Oval to rounded. Length: About 1 cm to 2 cm. Diameter: About 1 cm to 1.5 cm. Texture: Smooth, glabrous. Color: Close to 67A.

*Petals.*—Quantity and arrangement: Typically five in a single whorl; slightly imbricate. Length: About 1 cm to 1.5 cm. Width: About 5 mm to 10 mm. Shape: Obovate to elliptic. Apex: Obtuse. Base: Cordate. Margin: Entire; slightly undulate. Texture, upper and lower surfaces: Smooth, glabrous. Luster, upper and lower surfaces: Matte, satiny. Color: When opening and fully opened, upper surface: Close to 155C tinged with close to 64D. When opening and fully opened, lower surface: Close to 155C flushed with close to 67A.

*Sepals.*—Quantity and arrangement: Typically five in a single whorl. Length: About 5 mm to 7 mm. Width: About 3 mm to 5 mm. Shape: Ovate to somewhat deltoid. Apex: Acute to obtuse. Base: Cordate. Margin: Entire. Texture, upper and lower surfaces: Smooth, glabrous. Color, upper and lower surfaces: Close to 147C; towards the apex and base, tinged with close to 187A.

*Pedicels.*—Length: About 3 cm to 5 cm. Diameter: About 2 mm to 4 mm. Strength: Moderately strong. Aspect: About 60° to 90° from stem. Texture: Smooth, glabrous. Color: Close to 147C with spots, close to 187A.

*Reproductive organs.*—Stamens: Quantity: About 20 per flower. Filament length: About 2 cm. Filament color: Close to 155C. Anther length: About 3 mm to 5 mm. Anther shape: Bi-lobed. Anther color: Close to 17A. Pollen amount: Scarce. Pollen color: Close to 158A. Pistils: Quantity: About five per flower. Pistil length: About 1.5 cm. Stigma shape: Trumpet-shaped. Stigma color: Close to 154A. Style length: Less than 1 cm. Style color: Close to 150A. Ovary color: Close to 144A.

Fruit description:

*Ripening time.*—About 160 to 170 days.

*Yield.*—Higher than average.

*Use.*—Fresh market.

*Length.*—About 7 cm to 8 cm.

*Diameter*.—About 8.5 cm to 9 cm.

*Fruit weight*.—Typically individual fruits will weigh between 200 to 250 gr depending on environmental conditions.

*General shape in profile*.—Obloid.

*Depth of eye basin*.—Medium, about 1.2 cm.

*Width of eye basin*.—Medium, about 3 cm.

*Fruit stalk length*.—Medium to long.

*Fruit stalk diameter*.—About 2 mm.

*Fruit stalk color*.—Close to 176A.

*Fruit skin color*.—Ground color, close to 7A, overlain with close to 47A; at harvest, almost all of the fruit skin is red in color.

*Lenticels*.—Quantity: Numerous, about 10 per square inch. Length: About 2 mm to 3 mm. Color: Close to 153A.

*Flesh texture*.—Firm, compact.

*Flesh color*.—Close to 11A.

*Flavor*.—Rich, aromatic.

*Locules*.—Quantity per fruit: About five. Length: About 1.5 cm. Width: About 5 mm to 10 mm. Shape: Ovate.

*Seeds*.—Quantity per locule: None to about three depending on environmental conditions. Length: About 5 mm to 7 mm. Diameter: About 3 mm to 5 mm. Shape: Obovate to elliptic. Color: Close to 200A.

Temperature tolerance: The new Apple tree has been observed to tolerate temperatures ranging from about −20° C. to about 35° C.

Pathogen & pest resistance: Trees of the new Apple have been observed to be resistant to Apple Scab (*Venturia inaequalis*). Trees of the new Apple have not been observed to be resistant to pests and other pathogens common to Apple trees.

It is claimed:

1. A new and distinct Apple tree named 'WUR37' as illustrated and described.

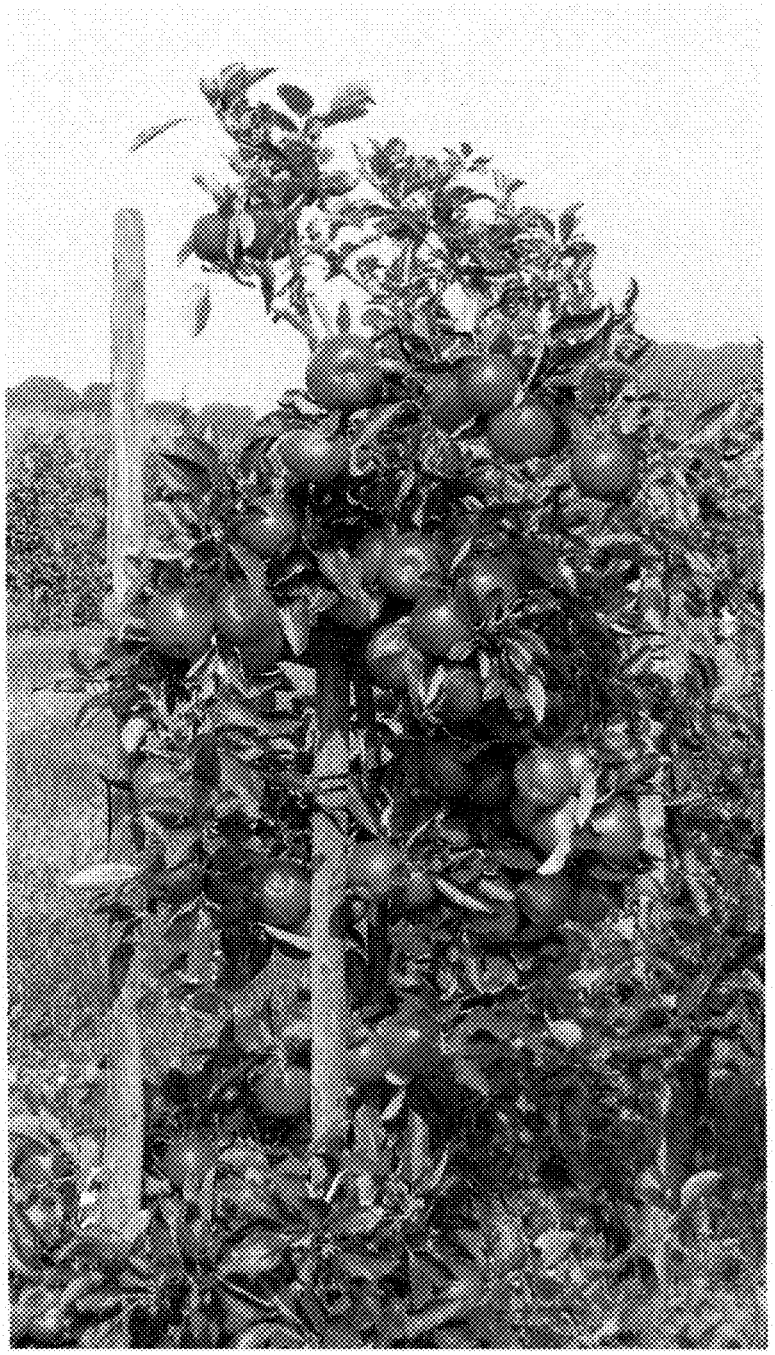

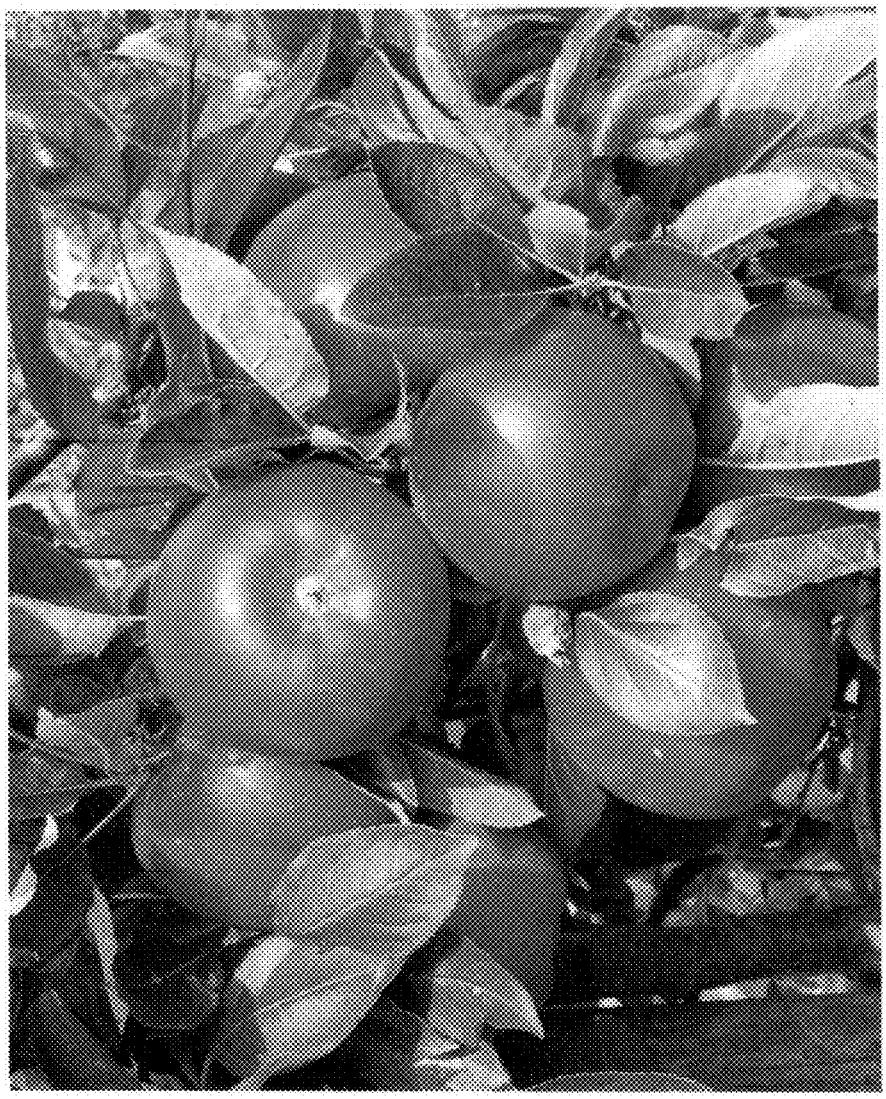

* * * * *